United States Patent
Smets et al.

(10) Patent No.: US 11,160,500 B2
(45) Date of Patent: Nov. 2, 2021

(54) SYSTEM AND METHOD FOR DETERMINING A SUBJECT'S STRESS CONDITION

(71) Applicants: IMEC VZW, Leuven (BE); Katholieke Universiteit Leuven, KU LEUVEN R&D, Leuven (BE); Stichting IMEC Nederland, Eindhoven (NL)

(72) Inventors: Elena Smets, Kessel-Lo (BE); Emmanuel Rios Velazquez, Nuenen (NL); Giuseppina Schiavone, Breda (NL); Walter De Raedt, Lint (BE); Christiaan Van Hoof, Heverlee (BE)

(73) Assignees: IMEC vzw, Leuven (BE); Katholieke Universiteit Leuven, KU LEUVEN R&D, Eindhoven (NL)

( * ) Notice: Subject to any disclaimer, the term of this patent is extended or adjusted under 35 U.S.C. 154(b) by 114 days.

(21) Appl. No.: 16/224,474

(22) Filed: Dec. 18, 2018

(65) Prior Publication Data

US 2019/0192074 A1    Jun. 27, 2019

(30) Foreign Application Priority Data

Dec. 21, 2017   (EP) .................................... 17209817

(51) Int. Cl.
*A61B 5/00*    (2006.01)
*G16H 50/20*   (2018.01)
(Continued)

(52) U.S. Cl.
CPC ............ *A61B 5/4884* (2013.01); *A61B 5/165* (2013.01); *A61B 5/7264* (2013.01); *A61B 5/742* (2013.01);
(Continued)

(58) Field of Classification Search
CPC ..... A61B 5/4884; A61B 5/165; A61B 5/7264; A61B 5/742; G16H 50/20; G06N 20/00
See application file for complete search history.

(56) References Cited

U.S. PATENT DOCUMENTS

2015/0073720 A1*  3/2015  Altini ...................... G06F 17/10
                                                                702/19
2015/0265211 A1   9/2015  Schneider et al.
(Continued)

OTHER PUBLICATIONS

Extended European Search Report and Written Opinion, EP Application No. 18212448.7, dated May 15, 2019, 9 pages.
(Continued)

*Primary Examiner* — Amanda K Hulbert
*Assistant Examiner* — Natasha Patel
(74) *Attorney, Agent, or Firm* — McDonnell Boehen Hulbert & Berghoff LLP

(57) ABSTRACT

Disclosed herein is a system for determining a subject's stress condition. The system includes a stress test unit configured for: receiving features defining the subject and physiological signals sensed from the subject when performing a relaxation and a stressful test task; extracting normalization parameters from the physiological signals; and identifying stress-responsive physiological features. The system also includes a storage unit configured for: storing a plurality of stress models; and storing the subject's features, normalization parameters, and the stress-responsive physiological features. The system also includes a stress detection unit configured for: selecting a stress model from the plurality of stress models based on the subject's features and the stress responsive physiological features; estimating a specific stress condition based on the stress model, stored subject's features, normalization parameters, and physiological signals that apply to the selected stress model; and providing a stress value representative of the subject's stress condition.

19 Claims, 4 Drawing Sheets

(51) Int. Cl.
   *G06N 20/00*   (2019.01)
   *A61B 5/16*    (2006.01)
(52) U.S. Cl.
   CPC ............ *G06N 20/00* (2019.01); *G16H 50/20* (2018.01); *A61B 2505/07* (2013.01)

(56) References Cited

U.S. PATENT DOCUMENTS

2017/0095157 A1*  4/2017  Tzvieli ................. A61B 5/0077
2018/0357915 A1* 12/2018  Harlow ................. G06N 7/005
2019/0336724 A1* 11/2019  Li ......................... A61B 5/486

OTHER PUBLICATIONS

Aigrain, Jonathan. "Multimodal detection of stress: evaluation of the impact of several assessment strategies." PhD diss., Paris 6, 2016.

\* cited by examiner

SYSTEM AND METHOD FOR DETERMINING A SUBJECT'S STRESS CONDITION

CROSS-REFERENCE TO RELATED APPLICATIONS

The present application is a non-provisional patent application claiming priority to EP 17209817.0, filed on Dec. 21, 2017, the contents of which are hereby incorporated by reference.

FIELD OF THE DISCLOSURE

The present description relates generally to electronic systems and methods for estimating a physiological and/or psychological stress condition experienced by living subjects, such as animal or human beings, using one or more of the subject's physiological signals and characteristic features. More specifically, it relates to electronic systems and a method for being implemented in such systems, which determine subject-specific stress values.

BACKGROUND

Stress-related events are important physical, mental, and/or emotional conditions that affect a subject in daily life and represent a considerable cost to public health and economy. The American Psychological Association states that in the US in 2015 24% of adults reported extreme stress conditions and reactions. Research has extensively revealed the negative consequences of stress, such as, for example, higher risks of health disorders (e.g., depression, heart rhythm disorders, diabetes, and cancer).

Some current methods of detecting stress make use of questionnaires that have to be filled by a certain user, e.g., a Job Content Questionnaire. However, these questionnaires are subjective, time consuming, and are conducted on spot-check basis only. Therefore, current research is focused on finding objective, continuous, and quantitative ways to detect stress using animal or human models and associated stress tests.

Earlier research has also shown, for example, that the physiological response of a subject to a stress situation is dependent upon or specific to that subject. That is, the type of physiological signal affected and the magnitude of the response to a stressful situation can vary from subject to subject. An example is shown in FIG. 1A, in which a first person A represents a subject who responds to stress with increasing heart rate (HR) and increasing skin conductance (SC), while, as can be seen in FIG. 1B, a second person B only responds to that stress situation with increasing HR (while the SC signal does not change specifically in response to the stressor).

In order to better detect the subject responses to stress, improving the current state of the art electronic systems and methods for determining a subject's stress condition is desirable.

SUMMARY

An improved system and method for determining a subject's stress condition is herein disclosed. The disclosure focuses on physiological stress detection based on one or more of the subject's physiological signals, such as, for example and not limited to, electrocardiogram (ECG), heart rate (HR), heart rate variability (HRV), blood volume pulse (BVP), skin conductance (SC) and/or skin temperature (ST).

The disclosure is defined by the claims.

According to an example embodiment, the electronic system may be useful for determining a subject's stress condition in ambulatory set ups.

According to another example embodiment, the electronic system may be able to determine a personalized or subject-specific stress response.

According to yet another example embodiment, the electronic system may be able to continuously or periodically determine personalized or subject-specific stress values during the subject's daily living conditions.

According to a further example embodiment, the electronic system may increase the accuracy of ambulatory stress detection.

According to another example embodiment, the proposed system and method may take personal or subject-specific differences into account, thereby providing stress level estimations with higher accuracy.

According to an example embodiment, physiology data may be recorded during a stress test to identify: a) which physiological features mostly correlate with stress response for a specific subject, and b) personalized or subject-specific data normalization parameters. This information may then be used to select an optimal stress model for a specific subject out of a stress model pool generated based on the stress data of a study population in specific conditions, e.g., daily life, where each model may have been trained with a different set of features.

According to an example embodiment, such personalized or subject-specific models can be used for stress detection with normalized relevant physiological features as input.

According to an example embodiment, the disclosure may use input data, namely anthropometric or characteristic features of the subject and physiological signals during a stress test and/or during daily life to output a stress value.

According to an example embodiment, the system may further comprise a reinforcement learning unit for adaptive learning of the subject's stress responses.

According to an example embodiment, a notification may be sent to the subject to ensure that the personalized stress model remains accurate. Such notification may be provided, for example, in the form of a text message, a value, or haptic feedback.

According to an example embodiment, notifications may be activated when a high stress event is detected or at desired time intervals.

According to an example embodiment, a stress event detection may trigger the repetition of the stress test and both relevant features and normalization parameters may be updated for the subject.

According to an example embodiment, a stress event detection may trigger a notification for confirmation of the detected stress level, which may update the models pool. The disclosure may be used both for determining and monitoring a stress condition of human and animal beings.

According to example embodiments, the system and method may be controlled or used by the subject or a third person in charge of the subject, e.g., in hospitals, animal or cattle management environments.

According to an example embodiment, an electronic system for determining a subject's stress condition according to claim 1 is provided.

The disclosure also relates to an electronic device comprising an electronic system for determining a subject's stress condition according to embodiments herein described.

The disclosure also relates to a method for determining a subject's stress condition according to claim 8.

The disclosure also relates to a computer readable storage medium according to claim 14.

BRIEF DESCRIPTION OF THE FIGURES

The above and other aspects of the system and method according to the present description will be shown and explained with reference to the non-restrictive example embodiments described hereinafter.

DETAILED DESCRIPTION

In the following, in the description of exemplary embodiments, various features may be grouped together in a single embodiment, figure, or description thereof for the purpose of streamlining the disclosure and aiding in the understanding of one or more of the various inventive aspects. This, however, is not to be interpreted as the disclosure requiring more features than the ones expressly recited in the main claim. Furthermore, combinations of features of different embodiments are meant to be within the scope of the disclosure, as would be clearly understood by those skilled in the art. Additionally, in other instances, well-known methods, structures and techniques have not been shown in detail in order not to obscure the conciseness of the description.

Figure 2:
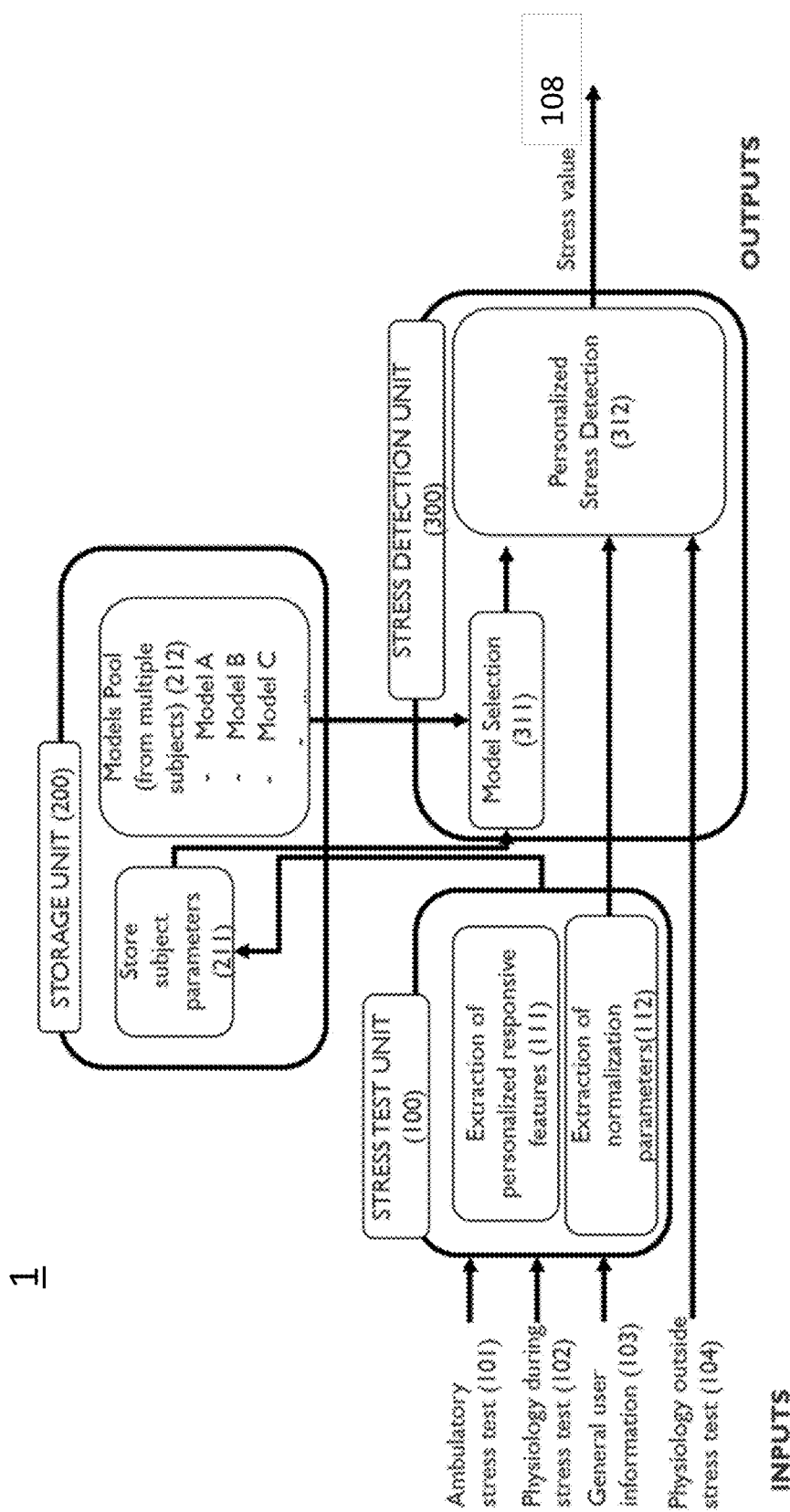
FIG. 2 shows a first a system for determining a subject's stress condition, according to an example embodiment.

FIG. 2 shows a first system 1 for determining a subject's stress condition, according to an example embodiment. As shown in FIG. 2, the system 1 comprises a stress test unit 100, a storage unit 200, and a stress detection unit 300. The stress test unit 100 may receive information when the subject is performing a stress test 101, which may consist of a baseline or relaxing task and a stressful task. Examples of stress tests include, but are not limited to, the Stroop Color Word Test and the Montreal Imaging Stress Task. The stress test unit 100 may also receive general information on the subject or characteristic features 103 of the subject, including, in some embodiments, gender, age, BMI, and/or anthropometric information.

Figure 1A:
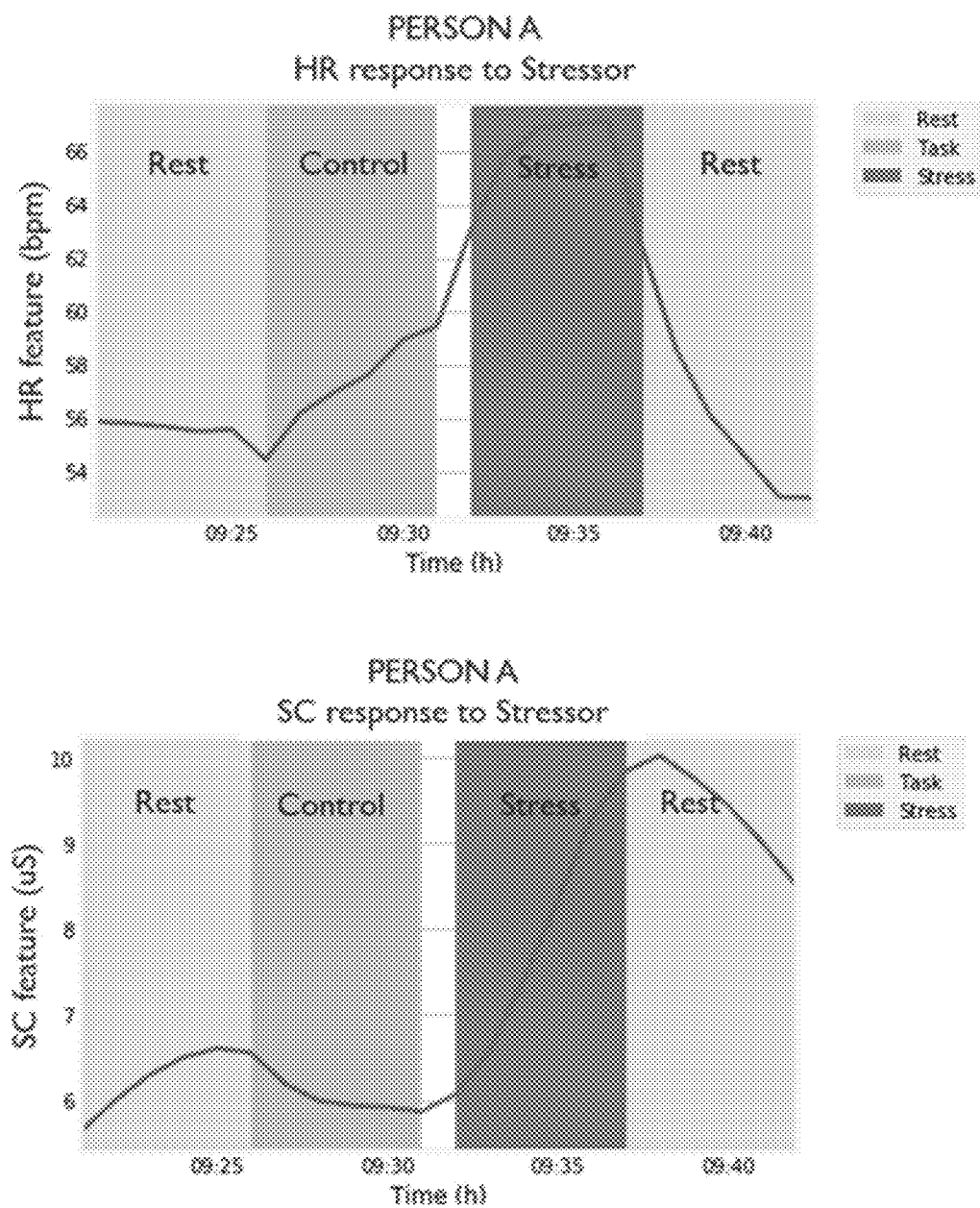
FIG. 1A shows a graph of a first person's heart rate (HR) and skin conductance (SC) during three different types of activities, according to an example embodiment.
Figure 1B:
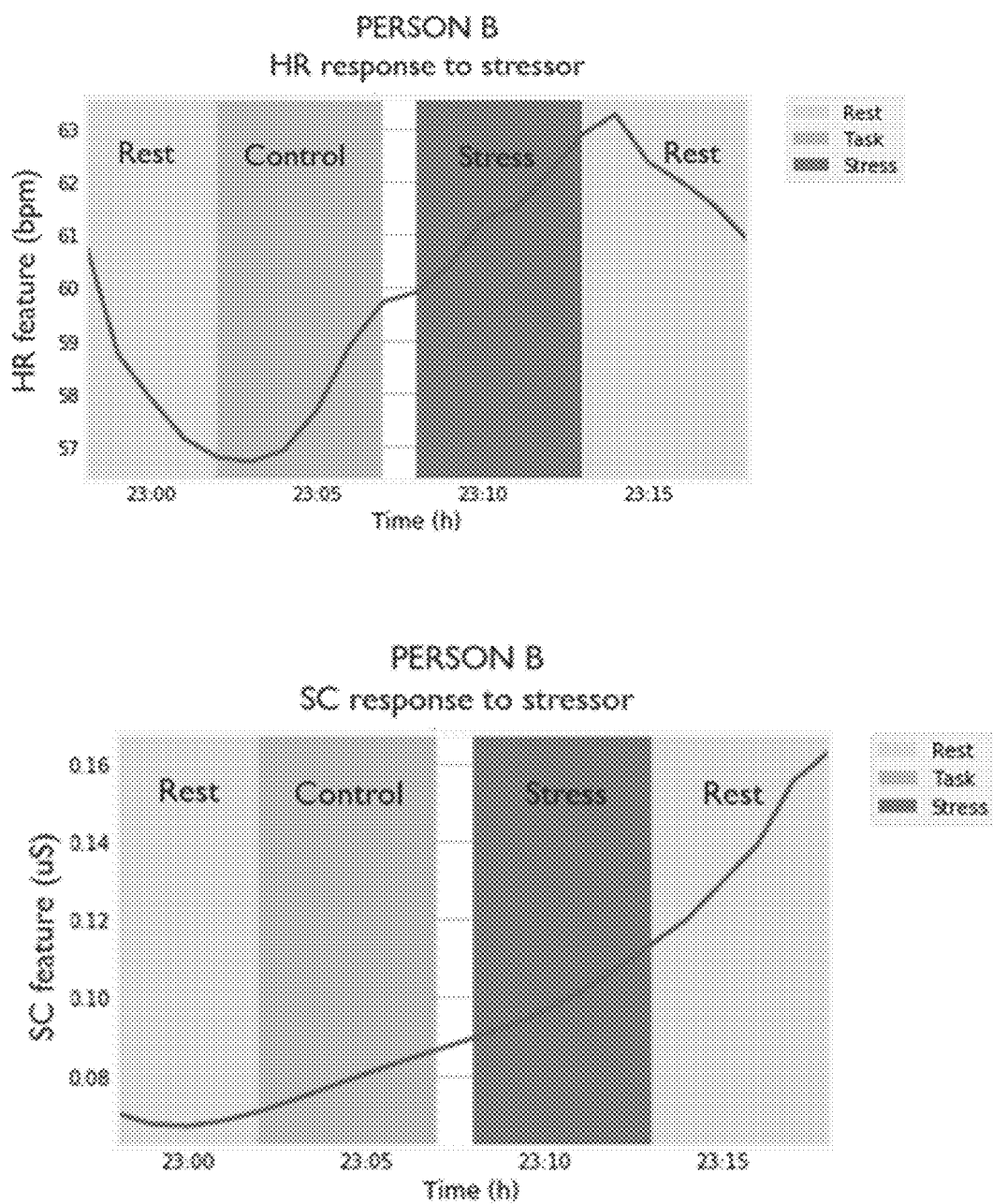
FIG. 1B shows a graph of a second person's heart rate (HR) and skin conductance (SC) during three different types of activities, according to an example embodiment.

The stress test unit 100 may further receive one or more physiological signals 102, for example, heart rate variability, heart rate, blood pressure and/or skin conductance, coming from a physiological signal sensor or sensing device, such as, for example, a wearable sensing device, a wired sensing device, or a device with non-contact sensing electrodes. The stress test unit 100 may further extract normalization parameters 112, such as, for example, mean and standard deviation or baseline physiology. Additionally, the stress unit 100 may identify the physiological features (e.g., heart rate, skin conductance, temperature, etc.) of the subject that are responsive during the stress test condition to the stress test 101. As illustrated in FIGS. 1A and 1B, the physiological stress response may be subject-dependent. In this operation, the subject-specific responsive-to-stress features may be identified. According to some embodiments, techniques such as correlation analysis, feature importance, and/or regression models may be used to obtain the subject's stress-responsive features 111 and the subject's normalization parameters 112.

The storage unit 200 may contain a pool of stress models 212 generated from a wider subject population. Each model may have been trained with a different set of features (e.g., physiological features and/or anthropometric parameters) using, for example, machine learning techniques, such as classification or regression analysis. A first model, Model A, may, for example, contain HR features, a second model, Model B, may contain skin conductance features, and a third model, Model C, may contain a combination of both, among other example models. The subject-specific or personal parameters 211, including normalization parameters, stress-responsive physiological signal feature sets, and general or characteristic subject information (e.g., anthropometrics) may be stored in the storage unit of the system.

The stress detection unit 300 may be configured for selecting a certain model 311 from the plurality or pool of stress models available in the storage unit 200. The model selected may be one in which the subject-specific stress-responsive features are used. With the selected model 311, the stored subject parameters 211 (including characteristic features, normalization parameters, and stress-responsive feature sets), and the subject's physiological signal data 104, the stress detection unit 300 may perform an estimation of the subject-specific stress condition. The subject's physiological signal data 104 may be physiological signal information that is gathered outside a stress test event, and may be, for example, physiological signal data during daily life. Based on that stress estimation, the stress detection unit 300 may provide stress values representative of the subject-specific stress condition.

Figure 3:
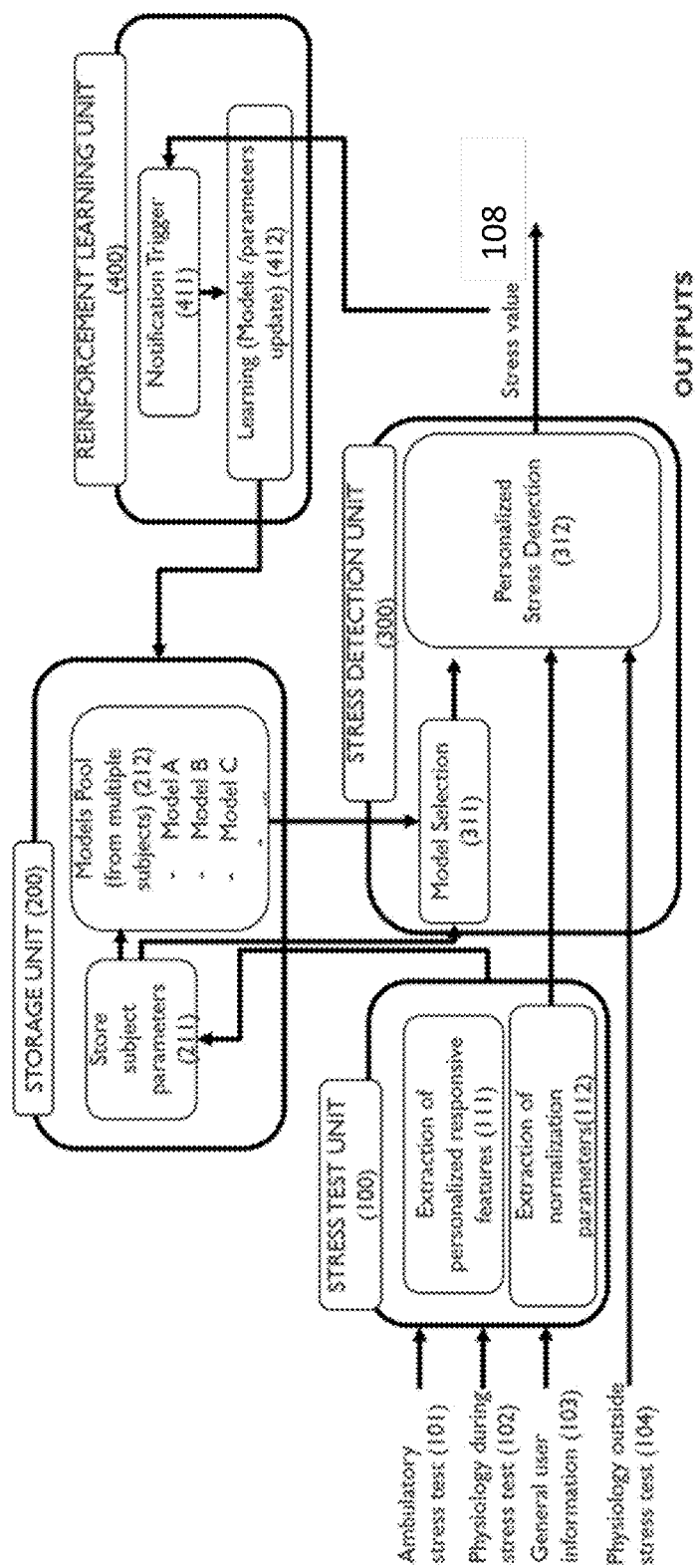
FIG. 3 shows a second system for determining a subject's stress condition, according to an example embodiment.

FIG. 3 shows a second system 2 for determining a subject's stress condition, according to an example embodiment. The system 2 further comprises (in comparison to system 1) a reinforcement learning unit 400. This reinforcement learning unit 400 may ensure accuracy over long-term use, given that normalization and relevant stress-responsive features may change for a subject over time, perhaps due to ageing, adaptation, or other life events. According to one embodiment, the stress value output 108, obtained, for example, during daily life, may trigger the reinforcement learning unit 400 to notify the subject 411 or a person in charge of the subject. According to an embodiment, the notification may, for example, ask the subject, or said person in charge of the subject, to confirm an estimated stress level. This subject information may then be used for learning operations 412, such as to update the stored stress models 212. According to an embodiment, it may also be used to request the subject, or the person in charge of the subject, to again perform the stress test in order to update stress models 212 and subject's parameters 211. In another embodiment, the trigger notification to repeat the test and keep high accuracy detection over time may be set by the user at a desired frequency.

It shall be noted that the systems for determining a subject's stress condition according to embodiments herein described may be implemented according to hardware and/or software state of the art techniques, comprising for example a microprocessor, microcontroller or digital signal processor that can understand and execute software program instructions. Some programmable hardware logic and memory means may be specifically designed also for executing the method or parts of it according to exemplary embodiments of the invention. It is also understood that the units of the system described may be implemented in distributed locations, for example in a mobile device and within a device network. The storage unit may be a single storage memory unit or a distributed memory unit.

What is claimed is:

1. An electronic system for determining a stress condition associated with a subject, the electronic system comprising:
   one or more processors; and
   a memory in communication with the one or more processors that stores instruction code that causes the electronic system to perform operations comprising:
      receiving one or more characteristic features defining the subject;
      receiving, in real-time from one or more sensors, one or more physiological signals sensed from the subject while the subject performs a baseline task and a stressful task that is different from the baseline task;
      determining normalization parameters based on the one or more physiological signals;
      identifying, from among a plurality of physiological features and based on the one or more sensed physiological signals, one or more physiological features that did respond to the stressful task;
      selecting, from among a plurality of machine learning stress models, a particular machine learning stress model trained to predict a subjects stress based on particular physiological features of the subject that did respond to the stressful task, wherein the plurality of machine learning stress models includes other machine learning stress models, each trained to predict a subject's stress based on a different set of physiological features, wherein a first set of physiological features includes a particular physiological feature that is not part of the physiological features of a second set of physiological features;
      inputting into a selected machine learning stress model, the characteristic features, the identified one or more physiological features that did respond to the stressful task, the normalization parameters, and the one or more sensed physiological signals; and
      receiving from the selected machine learning stress model a predicted stress value representative of the stress condition of the subject.

2. The electronic system of claim 1, wherein the operations further comprise
   based on information or physiological signals from the subject, updating one or more of: the normalization parameters, stress-responsive physiological features, or one or more of the plurality of machine learning stress models.

3. The electronic system of claim 2, wherein the operations further comprise:
   requesting the subject to perform a predetermined stressful task; and
   based on physiological features extracted from the subject's physiological signals sensed during that predetermined stressful task, updating the normalization parameters, stress-responsive physiological features, and/or one or more of the plurality of machine learning stress models.

4. The electronic system of claim 2, wherein the operations further comprise:
   requesting, from the subject, subject feedback indicative of a stress value;
   receiving, from the subject, the subject feedback; and
   based on the subject feedback, updating one or more of the plurality of machine learning stress models.

5. The electronic system of claim 4, wherein requesting, from the subject, subject feedback comprises:
   providing the subject with a notification that requests the subject feedback.

6. The electronic system of claim 2, wherein the operations further comprise:
   performing the updating at predetermined, or dynamically determined, time intervals or when the stress value reaches a predetermined, or dynamically determined, threshold.

7. The electronic system of claim 1, further comprising:
   a display device configured to display the predicted stress value.

8. A computer-implemented method for determining a subject's stress condition, the method comprising:
   receiving, by a computing device, one or more characteristic features defining the subject;
   receiving, in real-time by the computing device and from one or more sensors, one or more physiological signals sensed from the subject while the subject performs a baseline task and a stressful task that is different from the baseline task;
   determining, by the computing device, normalization parameters based on the one or more physiological signals;
   identifying, by the computing device, from among a plurality of physiological features and based on the one or more sensed physiological signals, one or more physiological features that did respond to the stressful task;
   selecting, by the computing device, from among a plurality of machine learning stress models, a particular machine learning stress model trained to predict a subjects stress based on particular physiological features of the subject that did respond to the stressful task, wherein the plurality of machine learning stress models includes other machine learning stress models, each trained to predict a subject's stress based on a different set of physiological features, wherein a first set of physiological features includes a particular physiological feature that is not part of the physiological features of a second set of physiological features;
   inputting, by the computing device and into a selected machine learning stress model, the characteristic features, the identified one or more physiological features that did respond to the stressful task, the normalization parameters, and the one or more sensed physiological signals; and
   receiving, by the computing device and from the selected machine learning stress model, a predicted stress value representative of the stress condition of the subject.

9. The method of claim 8, further comprising:
   based on information or physiological signals from the subject, updating, by the computing device, one or more of: the subject's features, the normalization parameters, stress-responsive physiological features or one or more of the plurality of machine learning stress models.

10. The method of claim 9, further comprising:
    performing the updating at predetermined, or dynamically determined, time intervals or when a stress value reaches a predetermined, or dynamically determined, threshold.

11. The method of claim 8, further comprising:
    requesting the subject to perform a predetermined stressful task; and based on physiological features extracted from the subject's physiological signals sensed during that predetermined stressful task, updating the normalization parameters, stress-responsive physiological features, and/or one or more of the plurality of machine learning stress models.

12. The method of claim 8, further comprising:
requesting, from the subject, subject feedback indicative of the stress value;
receiving, from the subject, the subject feedback; and
based on the subject feedback, updating one or more of the plurality of machine learning stress models.

13. The method of claim 8, wherein requesting, from the subject, subject feedback about the stress value comprises:
providing the subject with a notification that requests the subject feedback.

14. A non-transitory computer-readable medium having stored thereon program instructions that when executed by a processor cause a computing device to perform a set of functions for determining a subject's stress condition, the functions comprising:
receiving one or more characteristic features defining the subject;
receiving, in real-time from one or more sensors, one or more physiological signals sensed from the subject while the subject performs a baseline task and a stressful task that is different from the baseline task;
determining normalization parameters based on the one or more physiological signals;
identifying, from among a plurality of physiological features and based on the one or more sensed physiological signals, one or more physiological features that did respond to the stressful task;
selecting from among a plurality of machine learning stress models, a particular machine learning stress model trained to predict a subjects stress based on particular physiological features of the subject that did respond to the stressful task, wherein the plurality of machine learning stress models includes other machine learning stress models, each trained to predict a subject's stress based on a different set of physiological features, wherein a first set of physiological features includes a particular physiological feature that is not part of the physiological features of a second set of physiological features;
inputting into a selected machine learning stress model, the characteristic features, the identified one or more physiological features that did respond to the stressful task, the normalization parameters, and the one or more sensed physiological signals; and
receiving from the selected machine learning stress model a predicted stress value representative of the stress condition of the subject.

15. The non-transitory computer-readable medium of claim 14, wherein the set of functions further comprises:
based on information or physiological signals from the subject, updating one or more of: the subject's features, the normalization parameters, stress-responsive physiological features, or one or more of the plurality of machine learning stress models.

16. The non-transitory computer-readable medium of claim 15, wherein the set of functions further comprises:
performing the updating at predetermined, or dynamically determined, time intervals or when a stress value reaches a predetermined, or dynamically determined, threshold.

17. The non-transitory computer-readable medium of claim 14, wherein the set of functions further comprises:
requesting the subject to perform a predetermined stressful task; and
based on physiological features extracted from the subject's physiological signals sensed during that predetermined stressful task, updating the normalization parameters, stress-responsive physiological features, and/or one or more of the plurality of machine learning stress models.

18. The non-transitory computer-readable medium of claim 14, wherein the set of functions further comprises:
requesting, from the subject, subject feedback indicative of the stress value;
receiving, from the subject, the subject feedback; and
based on the subject feedback, updating one or more of the plurality of machine learning stress models.

19. The non-transitory computer-readable medium of claim 14, wherein requesting, from the subject, subject feedback about the stress value comprises:
providing the subject with a notification that requests the subject feedback.

* * * * *